US010349630B2

(12) United States Patent
Florczak

(10) Patent No.: US 10,349,630 B2
(45) Date of Patent: Jul. 16, 2019

(54) SYSTEM AND A METHOD FOR REAL TIME DETECTION OF THE POSITION AND BEHAVIOR OF A PLURALITY OF ANIMALS

(71) Applicant: GEA Farm Technologies GmbH, Bonen (DE)

(72) Inventor: Keld Florczak, Horsens (DK)

(73) Assignee: GEA Farm Technologies GmbH, Bönen (DE)

( * ) Notice: Subject to any disclaimer, the term of this patent is extended or adjusted under 35 U.S.C. 154(b) by 423 days.

(21) Appl. No.: 14/439,445

(22) PCT Filed: Oct. 28, 2013

(86) PCT No.: PCT/EP2013/072502
§ 371 (c)(1),
(2) Date: Apr. 29, 2015

(87) PCT Pub. No.: WO2014/067897
PCT Pub. Date: May 8, 2014

(65) Prior Publication Data
US 2015/0237833 A1 Aug. 27, 2015

(30) Foreign Application Priority Data
Oct. 31, 2012 (DK) .................................. 2012 70669

(51) Int. Cl.
*A01K 29/00* (2006.01)
*A61B 5/00* (2006.01)
(Continued)

(52) U.S. Cl.
CPC ......... *A01K 29/005* (2013.01); *A01M 31/002* (2013.01); *A61B 5/00* (2013.01);
(Continued)

(58) Field of Classification Search
CPC ..... A01K 29/005; A01M 31/002; H04W 4/02
(Continued)

(56) References Cited

U.S. PATENT DOCUMENTS 6,473,038 B2 10/2002 Patwari
7,009,561 B2 3/2006 Menache et al.
(Continued)

FOREIGN PATENT DOCUMENTS

CN 101694716 A1 4/2010
EP 0945060 A2 9/1999
(Continued)

OTHER PUBLICATIONS

International Search Report and Written Opinion in corresponding International Application No. PCT/EP2013/072502 dated Jan. 9, 2014.
(Continued)

*Primary Examiner* — Jack K Wang
(74) *Attorney, Agent, or Firm* — Smith Law Office; Jeffry W. Smith

(57) ABSTRACT

The present invention relates to a system and a method for real time detection of the position and behavior of a plurality of animals which system comprises radio transmitter tags carried by the animals, where sensors receives signal from the tags, which system based of time delay of received signals at the sensors from the tags, perform calculation the position of the animals. It is the first object of the invention to achieve real time position of animal in a limited area. The object can be fulfilled by letting the system comprise a computer bases real time position calculation of the position of the animals, which system comprises a plurality of fixed reference radio transmitter tags, which system continuously based of received signal from the reference tags performs a calibration of the measured position of the animals. By using
(Continued)

fixed reference radio transmitters together with tags that are performing equal radio transmission functions, it is possible by fixed placed sensors to receive first signals from the animal tags, but also signals from the fixed reference radio transmitter tags to perform an automatic calibration of all received signals from animals.

13 Claims, 2 Drawing Sheets

(51) Int. Cl.
*H04W 4/02* (2018.01)
*A01M 31/00* (2006.01)
*G08B 13/14* (2006.01)
*G08B 23/00* (2006.01)

(52) U.S. Cl.
CPC .............. *G08B 13/14* (2013.01); *G08B 23/00* (2013.01); *H04W 4/02* (2013.01)

(58) Field of Classification Search
USPC .............................. 340/573.2, 573.1; 600/300
See application file for complete search history.

(56) References Cited

U.S. PATENT DOCUMENTS

| | | | | |
|---|---|---|---|---|
| 2002/0010390 A1* | 1/2002 | Guice | ................... | A01K 11/008 600/300 |
| 2004/0260506 A1 | 12/2004 | Jones et al. | | |
| 2005/0020279 A1 | 1/2005 | Markhovsky et al. | | |
| 2005/0145187 A1* | 7/2005 | Gray | ................... | A01K 11/008 119/174 |
| 2006/0125627 A1* | 6/2006 | Gardner | ............... | A01K 11/007 340/539.1 |
| 2006/0259831 A1 | 11/2006 | Sohm et al. | | |
| 2007/0008150 A1* | 1/2007 | Hassell | ................ | A01K 11/006 340/573.1 |
| 2007/0040739 A1 | 2/2007 | Small | | |
| 2007/0268138 A1* | 11/2007 | Chung | .................. | G01S 5/0018 340/572.1 |
| 2008/0154138 A1 | 6/2008 | McQuilkin | | |
| 2009/0201169 A1 | 8/2009 | D'Hont et al. | | |
| 2011/0102154 A1 | 5/2011 | Hindhede | | |
| 2011/0187591 A1 | 8/2011 | Walker, Sr. | | |
| 2012/0238912 A1 | 9/2012 | Rajkondawar et al. | | |
| 2015/0110202 A1 | 4/2015 | Tucker et al. | | |
| 2015/0293205 A1 | 10/2015 | Sloth et al. | | |

FOREIGN PATENT DOCUMENTS

| | | |
|---|---|---|
| PA | 201270668 | 10/2012 |
| WO | 2002054100 A2 | 7/2002 |
| WO | 2006096932 A1 | 9/2006 |
| WO | 2007103886 A2 | 9/2007 |
| WO | 2008113556 A1 | 9/2008 |
| WO | 2009135493 A1 | 11/2009 |
| WO | 2010066429 A1 | 6/2010 |
| WO | 2010108496 A1 | 9/2010 |
| WO | 2014067896 A1 | 5/2014 |

OTHER PUBLICATIONS

International Search Report and Written Opinion for International Application No. PCT/EP2013/072495 dated Apr. 23, 2014.

* cited by examiner

SYSTEM AND A METHOD FOR REAL TIME DETECTION OF THE POSITION AND BEHAVIOR OF A PLURALITY OF ANIMALS

FIELD OF THE INVENTION

The present invention relates to a system and a method for real time detection of the position and behaviour of a plurality of animals held in one or more limited areas, which system comprises radio receiver/transmitter tags carried by the animals, which system comprises a plurality of sensors, which sensors receives signal from the radio receiver/transmitter tags carried by the animals, which system based of time or phase delay of received signals at the sensors from the radio receiver/transmitter tags placed at the animal, perform calculation the position of the animals.

BACKGROUND OF THE INVENTION

WO2010DK50065 discloses a system and a method for detecting the behaviour of a number of animals, such as cattle, where each animal carries at least a number of detectors, which detectors are communicating with at least a first processor carried by the animal, which first processor further communicates with a central processor. The object of the invention is to detect animal behaviour and transmit data concerning the animal behaviour to a computer system for further analysis of the data. This object can be achieved by a system and if the system and method are further modified by letting the animal carry an accelerometer and a gyroscope for detecting movement of the animal, which system comprises at least a short-range communication system for transmitting data from the first processor to the second central processor. By using an accelerometer and a gyroscope placed at an animal, this accelerometer and gyroscope can detect the behaviour of the animal.

It is the first object of the invention to achieve real time position of animal in a limited area. A further object is based of the real time position to analyse the behaviour of each of the animals.

SUMMARY OF THE INVENTION

The object can be fulfilled by a system as disclosed herein by letting the system comprise a computer bases real time position calculation of the position of the animals, which system comprises radio receiver/transmitter tags, which system comprises a plurality of fixed reference radio receiver/transmitter tags, which system performs a first calculation of the optimal placement of sensors in the restricted area, which system further performs a second calculation of the optimal placement of the fixed reference radio transmitter tags, which sensors and fixed reference radio transmitter tags are placed in the limited area according the computer calculation of the optimal position for the sensors and fixed reference radio transmitter tags, which system continuously based of received signal from the reference radio transmitter tags performs a calibration of the measured position of the animals.

By using fixed reference radio transmitters together with tags that are performing equal radio transmission functions, it is possible by fixed placed sensors to receive first signals from the animal tags, but also signals from the fixed reference radio transmitter tags and in that way by the computer system to perform an automatic calibration of all received signals from animals. At least two sensors must receive same signals from both the animal tag and the fixed tag. In that way, it is possible for the system by measuring run time or face difference for signals received. Because the tags have a fixed uplink rate, it is possible by run time difference or face difference in the received signals to form very precise calculation of the position of the animal tag. If more sensors are receiving the same signals, it is possible even to get a more precise position of the tag at the animal. Hereby can be achieved a very precise real time position indication of a number of animals placed in a restricted area such as in a barn. Because the real time position is indicated and afterwards stored in the computer system, it is possible by further data analyses to get a good indication of the behaviour of the animals placed in the restricted area or in the barn.

In a preferred embodiment for the invention the system is designed in the area and the sub area so each sensor is able to communicate with at lest one fixed reference radio transmitter tag. Hereby can achieved that each time one of the sensors receive a signal from one of the tags placed at the animals, the sensor will also receive at least one signal for one of the fixed reference tags. Thereby can the computer system for each received signal be able to perform an effective correction for any calculation failure of the detection of the animal tag which probably has been received at more sensors. Operating with runtime calculation or face different calculations for the electronic signals is critical, because in many situations the direct communication line is maybe not the signal that gives the most effective signal for the computer system afterwards. But if the signal received from the fixed radio receiver/transmitter tag has the same failure, it is easy for the system to correct the position of the fixed tag and perform the same correction of the animal tag. If that process is performed in more than one direction, because the signals are received at more sensors placed some distance from each other, it is able to perform a correction so to say in more than one dimension. Probably in the practical receiving data from a tag and afterwards receiving data from one of the fixed tags will always give a signal that is received at a plurality of sensors. It is up to the computer system to decide which of these signals are to be used. Weak signals detected from sensors maybe over relatively long distance probably also contain more noise than sensors placed relatively close to the fixed reference radio receiver tag or the radio receiver transmitter tag carried by an animal.

In a further preferred embodiment for the invention, the computer system generates at least one map indicating the restricted area and the sub area, which map indicate the position of the sensors, which map further indicates the actual position of the radio receiver/transmitter tags carried by the animals, which map further indicates the position of the reference radio receiver/transmitter tags. The map is generated in order to give a farmer, or any person who has access to a farm, an overview of for example a herd of cows or other animals which are placed in a restricted area or in a barn. The map will very easily indicate if animals are healthy and if they are walking, standing or sleeping as they are supposed to. Animals that are maybe not part of the herd, but animals standing alone indicate on the map that these animals maybe have to be further inspected. Combined with other computer input such as indication of eating time, sleeping time, walking time, it is possible in the case of each animal to get an overview of the health of that animal.

In a further preferred embodiment for the invention, a user has access to the system by a computer connection via the internet, whereby the computer connected to the system has access to at least the map. Hereby is achieved that it is possible from any computer with access to the internet to be able to get access to a farm computer in that way to get access to, for example, the map as previously described and further animal details. The computer system is so that as soon as access by internet is possible also a mobile phone connection is possible to connect to the computer system. Therefore, different computer platforms are available.

In a further preferred embodiment for the invention, a user has access to animal details for each animal monitored by the system. It is possible by the system to select a specific animal and get information relating to that animal. That can be done just from the map or by a total overview of all animals in the system. In fact, it is possible at the map to point to one animal and then reach data for that animal.

In a further preferred embodiment for the invention, the system perform an analysis of the behaviour of the animals, which system based of measured behaviour over defined time period divide the animals into two or more groups. Looking at the actual position of an animal over a longer period such as 6 or maybe 12 hours or maybe for an even longer period, it is possible to detect the behaviour of the animal. Because of different behaviour of animals, a selection into animal groups is possible. A great number of groups are in fact possible.

In a further preferred embodiment for the invention, at least a first group of animals are placed in a group of normal behaviour, and at least a second group of animal defined as high activity. At least selecting the animals in relation to activity is easy to perform in the computer system. The activity of each animal can be combined with activity the day before or maybe the week before and in that way it can be indicated, if the behaviour of the animal has changed from normal behaviour into high activity. The animals indicating high activity could be further subdivided into groups.

In a further preferred embodiment for the invention, the area and sub area are placed inside at least one barn. It is preferred that the pending patent application as described is used inside a barn, but it is not limited to indoor use. Placing the sensors inside the barn, it is important that the sensors are placed so high that the radio signals can pass above the animals. Also the fixed tags have to be placed at positions where these tags can be in line of sight radio communication with the sensors. In that way, it is possible to receive relatively good signal strength in the communication. Especially in barns, it is important that a software system that receives the signals is able to filter out signals which occur after signal reflection that can take place at every metal surface inside a barn. These reflective signals have a longer distance to travel and therefore a much longer time delay. Therefore, it is important that these signals are corrected. Otherwise, the position of an animal can be indicated more or less outside the barn.

The pending patent application further concerns use of a system for configuration and operation of a system as previous disclosed the system is used for analyzing time periods the animals spends by pluralities of activities, at least such as eating, sleeping or walking. The behaviour of the animals could be selected into zones such as at the watering trough, upon feeding, sleeping, definitive out, walk or an unknown group definition. Further selection into zones is also possible such as animals standing or walking.

The present invention also concerns a method for configuration and operation of a computer system as previously disclosed, which method performs detection of position and behaviour of a plurality of animals, which animals carries at least one radio receiver/transmitter tag, which method for implementing and operation of the computer system comprising at least the following sequence of steps:

a: define at least one limited area for detection of animals in the computer system,
b: divide the area into a number of sub areas in the computer system,
c: let the computer system calculate a number of sensors for as well the total area as the sub areas,
d: let the computer system calculate an optimal position for the sensors in the total area and the sub areas,
e: let the computer system define a number of fixed reference radio receiver/transmitter tags,
f: let the computer system calculate the optimal position for the fixed reference radio receiver/transmitter tag,
g: place the sensors and reference radio receiver/transmitter tags at the calculated positions,
h: install the system at the area and sub area,
i: perform a test of the system.
j: use the method for calculating actual position of the animals,
k: use the method for calculating behaviour of the animals.

By the method as described above, it is possible to install a system in a restricted area or in a barn. By the method, it is possible to indicate the actual position of each animal that is placed in the restricted area.

In a preferred embodiment for the invention, the method performs a continuously calibration of the position of the animals based on the measured position of one or more reference radio receiver/transmitter tags. Hereby is achieved that there is a continuous calibration of each single position measurement of an animal. In that way, very precise position detection is possible. Without the calibration performed, the position of detected animals could have a failure of more than one meter. By the system with a calibration of each measured signal, the position of an animal is very precise. Maybe it is possible in a restricted area to perform a measurement with a failure less than 10 centimeters.

In a further preferred embodiment for the invention, where each of the sensors are communicating with at lest one fixed reference radio receiver/transmitter tags. Especially with the number of fixed reference radio receiver tags, it is assured that each sensor will receive an uplink from at least one fixed tag. Thereby the calibration can be performed highly effectively.

In a further preferred embodiment for the invention, the method is used in at least one barn. It is possible to use the invention as previously described in a barn.

DETAILED DESCRIPTION OF THE INVENTION

Figure 1:
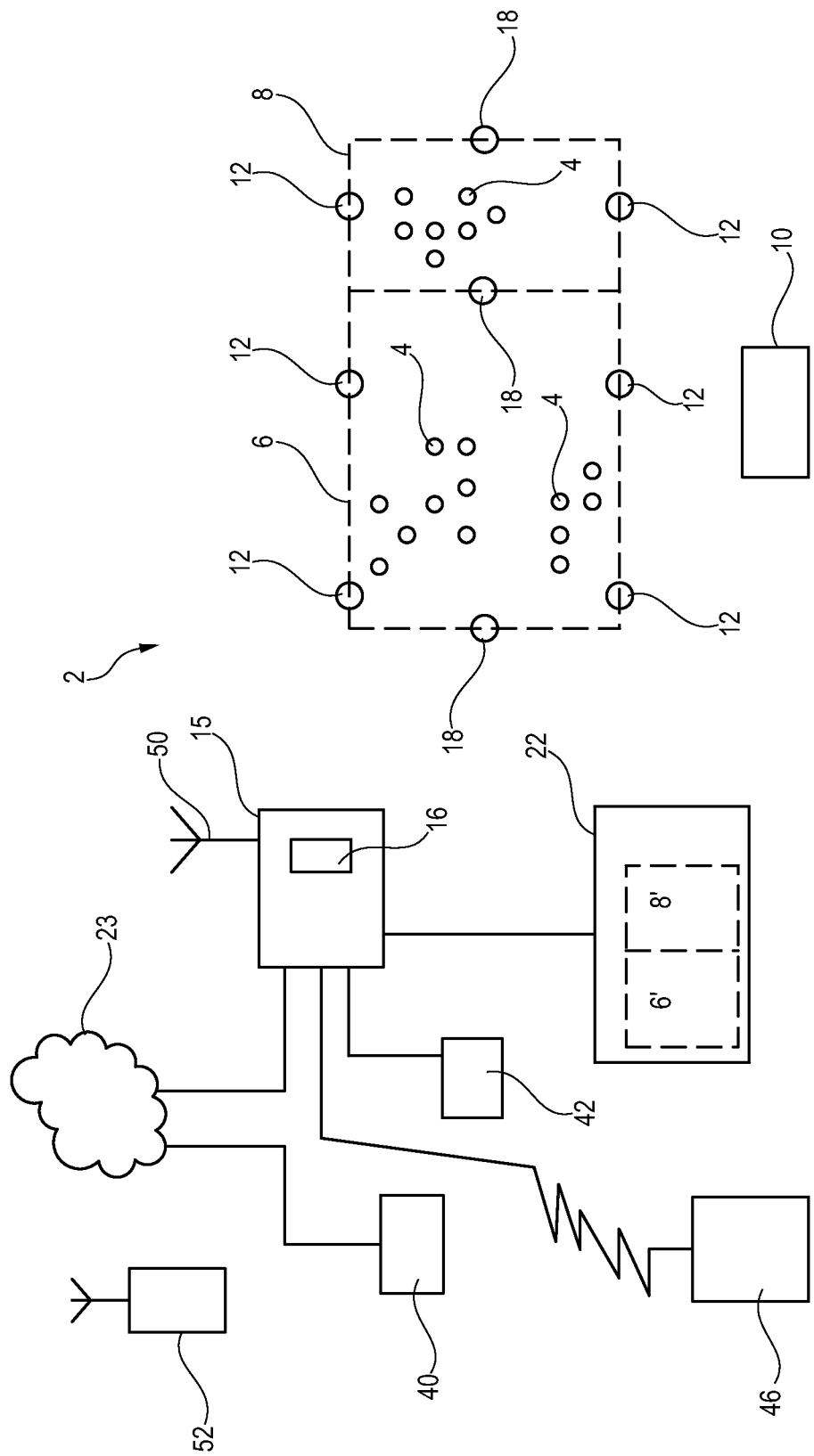
FIG. 1 discloses a possible embodiment for a system.

FIG. 1 discloses a possible embodiment for a system 2, which system comprises a restricted area 6 and/or a restricted sub area 8. In the restricted area 6,8 is indicated animals 4. These animals all carry a transmitter tag 10 which in a preferred version transmit a signal with time intervals controlled in the software of the tag. That means the tag 10 may transmit a signal one or more times per second. The system 2 further comprises a plurality of sensors 12 here indicated at the border of the restricted area 6,8. Further is indicated fixed reference tags 18 here indicated in the middle of the restricted area 6,8. The system further comprises a farm server 15 which farm server comprises a position detection system 16. The system 2 generates a map 22 which map 22 shows the restricted area 6',8' and not shown, but in practice indicating the animals 4 at the map. The farm server 15 is further connected to the internet 23 and through the internet 23 there is a connection to any computer 40 that has a necessary logon access into the farm server 15. Further is the farm server 15 connected over maybe an optical fibre connection to a back end computer 46. The farm server 15 further has wireless communication system 50 for connecting mobile devises 52, but once again communication is only performed to mobile devises having the necessary logon information ready, so it is more or less a closed communication from the mobile devise 52 to the mobile interface 50 and into the computer 15.

In operation, the backend computer 46 by installing a new system will perform a calculation of at first the necessary number of sensors 12 for a restricted area 6,8 or a barn 24 and the computer system 46 will also calculate the placement of sensors 12. Afterwards will the computer system 46 calculate the necessary reference tags and their placement in the restricted area 6,8 or the barn 24. Afterwards an installing process is performed where the sensors 12 and the reference tags 18 have to be placed as already indicated from the backend computer 46. The installing process also performs the installation of the server 15, and the connection of that server to the internet and by the wire communication or optical fibre communication or any other form for communication to the backend computer 46. Hereafter can a test be performed at first without tagged animals in the restricted area 6,8 and afterwards can animals 4 carrying the tag 10 be placed in the restricted area 6,8. The system will hereafter perform a indication of the position of the animals 4 several times per second. Because the sensors 12 together with signals from tags 10 will receive signals from the fixed tags 18, the system is able to perform calibration of the measured positions. The computer system 15 can after a short measuring period analyse the activity of the animals 4. At relatively long time intervals, the server 15 can transmit a report into the backend computer 46. This backend computer 46 can then perform analysis of the behaviour of the animals. This backend computer can then generate rather complicated report without help from the farm server 15.

Figure 2:
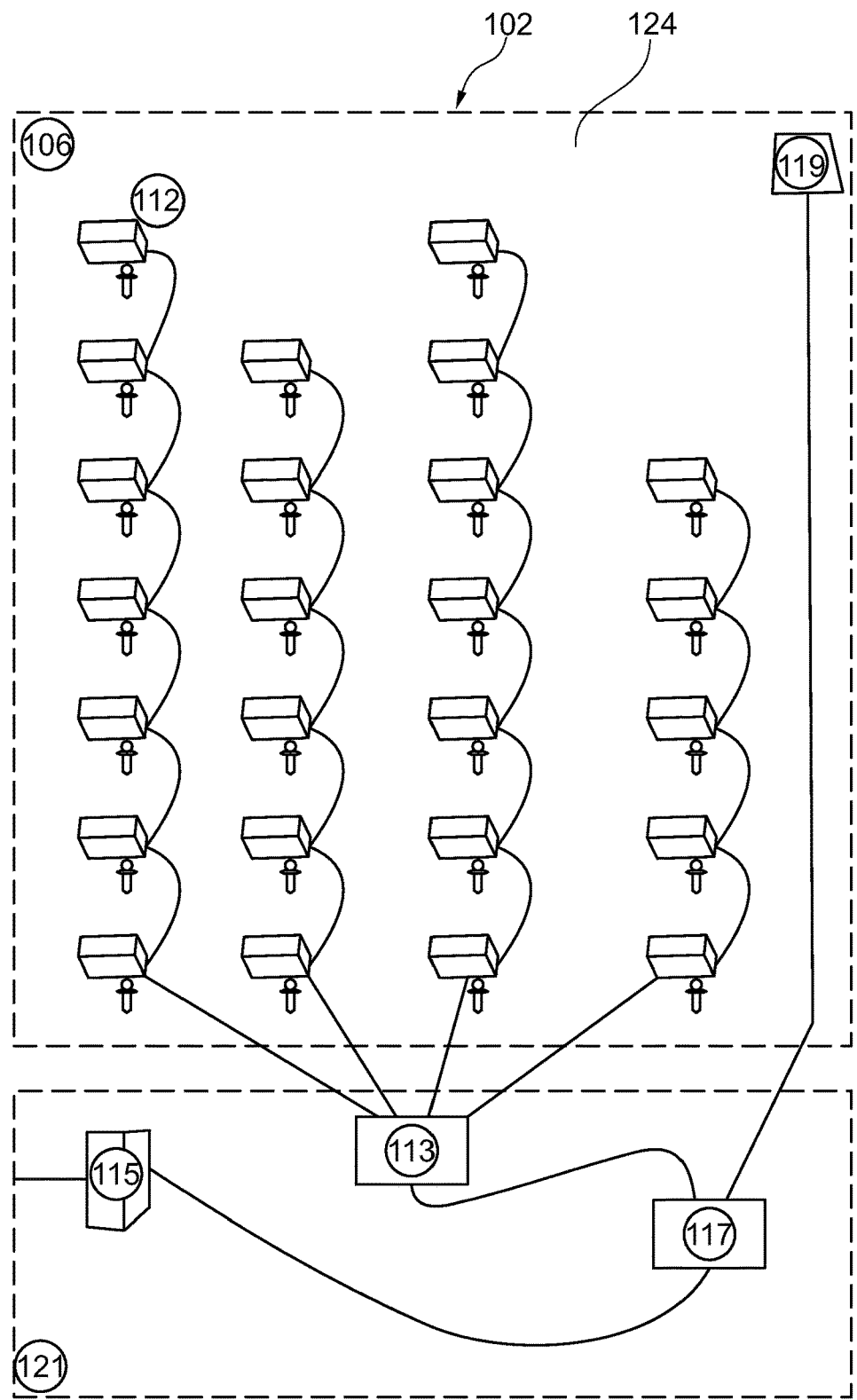
FIG. 2 shows a preferred embodiment for the invention.

FIG. 2 shows a further possible embodiment for the invention by a system 102. The system 102 is indicated as operating in a restricted area 106 or a barn 124. The system comprises a number of sensors 112 which are placed in the restricted area 106. These sensors 112 are all connected to a hub 113 which hub 113 is further connected to a switch 117. The switch 117 is further connected to a wireless access point 119. The switch 117 is further connected to a farm processor 115 which farm processor together with the hub 113 and the switch 117 are placed in a technical room 121 placed nearby the restricted area 106 or the barn 124. The farm computer 115 can perform communication to a backend computer such as indicated at the FIG. 1 as 46.

In operation all the system can perform measurement of the position of not shown animals in the restricted area 106 or the barn 124. Some parameters in the tags 10 (FIG. 1) carried by the animals are programmable and by the system, it is possible to get in contact with the tags carried by all animals. In that way, changes in a programme can be performed. One of the parameters which can be adjusted is the time period between when the tags perform a transmission. It is possible by a fast computer system to increase the number of transmissions from the tags by reprogramming.

The invention claimed is:

1. A system for real time detection of the position of a plurality of animals held in a limited area, the system comprising:
   a fixed reference radio transmitter tag disposed in the limited area;
   a plurality of radio receiver/transmitter animal tags capable of being carried by animals moving in the limited area;
   a sensor, in wireless communication with the fixed reference radio transmitter tags and the radio receiver/transmitter animal tags, based on a time or a phase delay of received signals at the sensors from the radio receiver/transmitter animal tags;
   a position detector comprising:
      a computer that calculates an optimal placement of the sensor for communicating with the radio receiver/transmitter animal tags and the fixed reference radio transmitter tag in the limited area; and for calculating an optimal placement of the fixed reference radio transmitter tag, and then receives a signal from the fixed reference radio transmitter tag to calibrate the system and then measure a position of at least one of the radio receiver/transmitter animal tags.

2. The system of claim 1, and further comprising:
   a second sensor positioned to receive data from the fixed reference radio transmitter tag and the radio receiver/transmitter animal tags.

3. The system of claim 1, wherein the position detector generates at least one map indicating the position of the radio receiver/transmitter animal sensors, and the position of the fixed reference radio transmitter tag.

4. The system of claim 3, and further comprising:
   an internet connection in communication with the position detector and having access to the map.

5. The system of claim 4, wherein the position detector stores data for individual animals associated with each radio receiver/transmitter animal tag, and the data is accessible via the internet.

6. The system of claim 5, wherein the position detector records animal tag position data over a time period to divide the animals into two or more groups based on the animal tag position data.

7. The system of claim 6, wherein a first group of animals is categorized in a group having normal behavior, and a second group is categorized in a group having abnormal activity.

8. The system of claim 1, wherein the limited area is disposed inside at least one barn.

9. The system of claim 1, wherein the position detector analyzes animal tag position data over a plurality of time periods to determine where the animal tags remain for periods of time and whether the animal tags are moving.

10. A method for configuration and operation of an animal position detector system for detecting positions of a plurality of animals, with each animal carrying at least one radio receiver/transmitter tag, the method comprising the following steps:
   a: defining at least one limited area for the animals to be detected in the animal position detection system,
   b: dividing the limited area into a number of sub areas,
   c: calculating a number of sensors for monitoring the limited area;
   d: calculating an optimal position for each sensor;
   e: defining a number of fixed reference radio receiver/transmitter tags;

f: calculating an optimal position for each fixed reference radio receiver/transmitter tag;
g: installing each sensor and each fixed reference radio receiver/transmitter tag at its calculated optimal position within the area and sub area;
h: performing a calibration test of the system by sensing signals from the fixed reference radio receiver/transmitter tag;
i: calculating an actual position of at least one animal carrying a radio receiver/transmitter tag; and
j: calculating activity of at least one animal.

11. The method of claim 10, wherein the animal position detection system continuously calculates a position of the animal based on the measured position of a reference radio receiver/transmitter animal tag.

12. The method of claim 10, wherein each sensor communicates with at least one fixed reference radio receiver/transmitter tag.

13. The method of claim 10, wherein the area is disposed in at least one barn.

\* \* \* \* \*